United States Patent [19]

Ahluwalia et al.

[11] Patent Number: 5,468,476
[45] Date of Patent: Nov. 21, 1995

[54] REDUCTION OF HAIR GROWTH

[76] Inventors: Gurpreet S. Ahluwalia, 8632 Stable View Ct., Gaithersburg, Md. 20879; Douglas Shander, 16112 Howard Landing Dr., Gaithersburg, Md. 20878; James P. Henry, 6776 Wood Duck Ct., Frederick, Md. 21701

[21] Appl. No.: 213,931

[22] Filed: Mar. 16, 1994

[51] Int. Cl.$^6$ .............. A61K 7/06; A61K 7/15; A61K 7/155
[52] U.S. Cl. .............. 424/73; 8/94.16; 435/265; 514/557; 514/844; 514/852; 514/880; 424/70.1; 424/62; 424/69
[58] Field of Search .............. 424/70.1, 73

[56] References Cited

U.S. PATENT DOCUMENTS

| | | | |
|---|---|---|---|
| 3,426,137 | 2/1969 | Philpitt et al. | 424/330 |
| 4,039,669 | 8/1977 | Beyler et al. | 424/243 |
| 4,139,638 | 2/1979 | Neri et al. | 424/324 |
| 4,161,540 | 7/1979 | Neri et al. | 424/324 |
| 4,191,775 | 3/1980 | Glen | 424/304 |
| 4,269,831 | 5/1981 | Ferrari et al. | 424/241 |
| 4,344,941 | 8/1982 | Wiechert et al. | 424/243 |
| 4,370,315 | 1/1983 | Greff et al. | 424/94 |
| 4,439,432 | 3/1984 | Peat | 424/240 |
| 4,720,489 | 1/1988 | Shander | 514/171 |
| 4,885,289 | 12/1989 | Breuer et al. | 514/170 |
| 5,095,007 | 3/1992 | Ahluwalia | 514/23 |
| 5,096,911 | 3/1992 | Ahluwalia et al. | 514/380 |
| 5,132,293 | 7/1992 | Shander et al. | 514/46 |
| 5,143,925 | 9/1992 | Shander et al. | 514/378 |
| 5,271,942 | 12/1993 | Heverhagen | 424/451 |

FOREIGN PATENT DOCUMENTS

| | | |
|---|---|---|
| 413528 | 2/1991 | European Pat. Off. |
| 0446699A1 | 9/1991 | European Pat. Off. |
| 0532219A2 | 3/1993 | European Pat. Off. |
| 1458349 | 12/1976 | United Kingdom |

OTHER PUBLICATIONS

Yu et al. CA. 115:189747F of EP 413528 (Feb. 20, 1991) (describes homoarginine for scalp and for skin (dandruff, skin disorders).

Messenger, The Journal of Investigative Dermatology, vol. 101, No. 1, Supplement, Jul. 1993, pp. 4S–9S.

Sato, Biology and Disease of the Hair, 1975, pp. 3–13.

Moncada et al., Pharmacological Reviews, vol. 43, No. 2, 1991, pp. 109–142.

Rees et al., Br. J. Pharmacol. (1990), 101, 746–752.

Radermacher et al., Effect of Arginine Depletion on Glomerular and Tubular Kidney Function: Studies in Isolate Perfused Rat Kidneys, 1991, pp. F779–F786.

Olken et al., J. Med. Chem., 1992, 35, 1137–1144.

McCall et al., Br. J. Pharmacol. (1991), 102, 234–238.

Stuehr et al., The FASEB Journal, vol. 5, Jan., 1991, pp. 98–103.

Simpson et al., Bristish Journal of Dermatology, (1979) 100, 687–692.

Burdick et al., Br. J. Derm. (1970) 82, Supplement 6, 19–25.

Goos et al., Arch. Dermatol. Res. (1982) 273:333–341.

Girard et al., Arch. Dermatol. Res. 269, 281–290 (1980).

Champion, The Medical Journal of Australia, vol. 149, No. 4, Aug. 15, 1988, pp. 203–213.

*Primary Examiner*—Shep K. Rose
*Attorney, Agent, or Firm*—Fish & Richardson

[57] ABSTRACT

Mammalian hair growth is reduced by applying to the skin an inhibitor of nitric oxide synthetase.

25 Claims, No Drawings

REDUCTION OF HAIR GROWTH

The invention relates to a method of reducing unwanted hair growth in mammals.

A main function of mammalian hair is to provide environmental protection. However, that function has largely been lost in humans, in whom hair is kept or removed from various parts of the body essentially for cosmetic reasons. For example, it is generally preferred to have hair on the scalp but not on the face.

Various procedures have been employed to remove unwanted hair, including shaving, electrolysis, depilatory creams or lotions, waxing, plucking, and therapeutic antiandrogens. These conventional procedures generally have drawbacks associated with them. Shaving, for instance, can cause nicks and cuts, and can leave a perception of an increase in the rate of hair regrowth. Shaving also can leave an undesirable stubble. Electrolysis, on the other hand, can keep a treated area free of hair for prolonged periods of time, but can be expensive and painful, and it sometimes causes scarring. Depilatory creams, though effective, typically are not recommended for frequent use due to their high irritancy potential. Waxing and plucking can cause pain, discomfort, in-grown hairs, and poor removal of short hair. Finally, antiandrogens—which have been used to treat female hirsutism—can have unwanted side effects.

It has previously been disclosed that the rate and character of hair growth can be altered by applying to the skin inhibitors of certain enzymes. These inhibitors include inhibitors of 5-alpha reductase, ornithine decarboxylase, S-adenosylmethionine decarboxylase, gamma-glutamyl transpeptidase, and transglutaminase. See, for example, Breuer et al., U.S. Pat. No. 4,885,289; Shander, U.S. Pat. No. 4,720,489; Ahluwalia, U.S. Pat. No. 5,095,007; Ahluwalia et al., U.S. Pat. No. 5,096,911; Shander et al., U.S. Pat. No. 5,132,293; and Shander et al., U.S. Pat. No. 5,143,925.

Nitric oxide synthetase forms nitric oxide by oxidizing one of the two terminal guanido nitrogens in L-arginine. The nitric oxide formed by the action of this enzyme is implicated in diverse physiological functions, including smooth muscle relaxation, immune system regulation, and neurotransmission.

It has now been found that unwanted mammalian (including human) hair growth, particularly androgen-stimulated hair growth, can be reduced by topical application of an inhibitor of nitric oxide synthetase to the skin. The unwanted hair growth which is reduced may be normal hair growth, or hair growth that results from an abnormal or diseased condition.

Preferred inhibitors of nitric oxide synthetase include $N^G$-methyl-L-arginine, $N^G$-nitro-L-arginine, $N^G$-nitro-L-arginine methyl ester, $N^G$-nitro-L-arginine benzyl ester, N-acetyl-L-arginine, $N^G$-amino-L-arginine, N-benzoyl-L-arginineamide, N-benzoyl-L-arginine methyl ester, N-benzoyl-L-arginine ethyl ester, $N^G$-allyl-L-arginine, $N^G$-cyclopropyl-L-arginine, N-iminoethyl-L-ornithine, L-homoarginine, L-argininamide, diphenyleneiodonium, iodonium-diphenyl, and di-2-thienyliodonium. Irreversible inhibitors of nitric oxide synthetase are preferred, although reversible inhibitors (competitive and non-competitive) also can be used.

The inhibitor of nitric acid synthetase preferably is incorporated in a topical composition which includes a non-toxic dermatologically acceptable vehicle or carrier which is adapted to be spread upon the skin. Examples of suitable vehicles are acetone, alcohols, or a cream, lotion, or gel which can effectively deliver the active compound. One such vehicle is disclosed in co-pending application PCT/US 93/0506A. In addition, a penetration enhancer may be added to the vehicle to further enhance the effectiveness of the formulation.

The concentration of the nitric oxide synthetase inhibitor in the composition may be varied over a wide range up to a saturated solution, preferably from 0.1% to 30% by weight or even more; the reduction of hair growth increases as the amount of inhibitor applied increases per unit area of skin. The maximum amount effectively applied is limited only by the rate at which the inhibitor penetrates the skin. Generally, the effective amounts range from 100 to 3000 micrograms or more per square centimeter of skin.

The composition should be topically applied to a selected area of the body from which it is desired to reduce hair growth. For example, the composition can be applied to the face, particularly to the beard area of the face, i.e., the cheek, neck, upper lip, and chin. The composition can also be applied to the legs, arms, torso or armpits. The composition is particularly suitable for reducing the growth of unwanted hair in women suffering from hirsutism or other conditions. In humans, the composition should be applied once or twice a day, or even more frequently, for at least three months to achieve a perceived reduction in hair growth. Reduction in hair growth is demonstrated when the frequency or hair removal is reduced, or the subject perceives less hair on the treated site, or quantitatively, when the weight of hair removed by shaving (i.e., hair mass) is reduced.

Male intact Golden Syrian hamsters are considered acceptable models for human beard hair growth in that they display oval shaped flank organs, one on each side, each about 8 mm. in major diameter, which grow thick black and coarse hair similar to human beard hair. These organs produce hair in response to androgens in the hamster. To evaluate the effectiveness of a particular nitric oxide synthetase inhibitor, the flank organs of each of a group of hamsters are depilated by applying a thioglycolate based chemical depilatory (Surgex). To one organ of each animal 10 µl. of vehicle alone once a day is applied, while to the other organ of each animal an equal amount of vehicle containing a nitric oxide synthetase inhibitor is applied. After thirteen applications (one application per day for five days a week), the flank organs are shaved and the amount of recovered hair (hair mass) from each is weighed. Percent-reduction of hair growth is calculated by subtracting the hair mass (mg) value of the test compound treated side from the hair mass value of the vehicle treated side; the delta value obtained is then divided by the hair mass value of the vehicle treated side, and the resultant number is multiplied by 100.

The above-described assay will be referred to herein as the "Golden Syrian hamster" assay. Preferred compositions provide a reduction in hair growth of at least about 35%, more preferably at least about 50%, and most preferably at least about 70%, when tested in the Golden Syrian hamster assay.

A number of nitric oxide synthetase inhibitors were tested in the Golden Syrian hamster assay. The results are presented in Table 1.

TABLE 1

| Compound | Dose | Vehicle | pH | Hair Mass | | Percent Reduction (mean ± SEM) |
| --- | --- | --- | --- | --- | --- | --- |
| | | | | Treated (mg) | Control (mg) | |
| $N^G$-methyl-L-arginine | 20% | A | 8.0 | 0.534 ± 0.06 | 2.291 ± 0.15 | 76.72 ± 2.63 |
| $N^G$-nitro-L-arginine methyl ester | 10% | A | 7.0 | 0.964 ± 0.17 | 2.765 ± 0.32 | 63.49 ± 6.41 |
| $N^G$-nitro-L-arginine methyl ester | 20% | A | 6.5 | 0.486 ± 0.13 | 2.856 ± 0.24 | 83.26 ± 2.76 |
| $N^G$-nitro-L-arginine benzyl ester | 15% | A | 7.0 | 1.045 ± 0.11 | 2.334 ± 0.12 | 54.70 ± 4.87 |
| $N\alpha$-acetyl-L-arginine | 10% | A | 4.0 | 1.274 ± 0.20 | 1.936 ± 0.09 | 33.12 ± 11.0 |
| $N\alpha$-benzoyl-L-arginine | 5% | B | 5.0 | 1.385 ± 0.16 | 2.391 ± 0.37 | 39.62 ± 4.02 |
| $N\alpha$-benzoyl-L-argininamide | 15% | B | 7.0 | 1.031 ± 0.11 | 1.973 ± 0.20 | 46.22 ± 5.03 |
| $N\alpha$-benzoyl-L-arginine methyl ester | 15% | B | 7.0 | 1.306 ± 0.21 | 2.656 ± 0.21 | 51.28 ± 8.26 |
| L-homoarginine | 20% | A | 5.5 | 1.189 ± 0.13 | 1.918 ± 0.13 | 37.79 ± 5.01 |
| L-argininamide | 20% | A | 5.0 | 0.669 ± 0.15 | 2.329 ± 0.23 | 67.69 ± 8.75 |

Vehicle A: Pure water (68%), ethanol (16%), propylene glycol (5%), dipropylene glycol (5%), benzyl alcohol (4%) and propylene carbonate (2%)
Vehicle B: Pure water (80%), ethanol (10%) and propylene glycol (10%)

The following assay measures the activity of nitric oxide synthetase in hair follicles. The assay can be used to evaluate the effectiveness of nitric oxide synthetase inhibitors in reducing nitric oxide synthetase activity.

Hair follicles from hamster flank organ were excised, and an enzyme extract was prepared in buffered sucrose solution, pH 7.4, using a sonicator device. The sonicated extracts were centrifuged at 12,000× g, and the clarified supernatant was analyzed for nitric oxide synthetase activity. Specifically, 50 μl of follicle supernatant were added to 150 μl of an assay mixture containing 100 mM tris buffer (pH 7.5), 50 μM cold arginine, 1 μCi/ml [$^3$H]-arginine, 3 mM CaCl$_2$, and 1 mM NADPH warmed to 37° C., and incubated for 30 minutes at 37° C. Formation of the radiolabelled citrulline, a coproduct of nitric oxide synthetase action that can be used to provide a measure of the enzyme activity, was determined using an HPLC methodology capable of separating citrulline from arginine.

More specifically, after termination of the enzyme reaction by heating at 95° C. for 5 min, the reaction mixture was centrifuged at 12,000× g for 2 min. A 100 μl aliquot of the clarified supernatant containing reaction products was injected onto a cation exchange column (10 μ Partisil 10-SAX 25 cm×4.6 mm), and then eluted with 0.02M monobasic potassium phosphate buffer (pH 4.5). Under these conditions the elution time of citrulline and arginine are 6 and, respectively. The HPLC effluent was collected in 1.0 ml fractions and the amount of radiolabelled citrulline formed in the assay was determined by scintillation counting. The enzyme activity was linear with respect to hair follicle extract added (i.e., protein concentration), as well as the time of incubation.

Inhibitors of nitric oxide synthetase were evaluated as follows. Inhibitors at a final concentration of 1.0 mM were preincubated with the hair follicle enzyme extract (the supernatant). The enzyme activity following exposure to the inhibitor was assayed as described above. This assay will be referred to herein as the "hair follicle nitric oxide synthetase inhibition assay." The results are provided in Table 2.

TABLE 2

| Test Compound | Inhibition of Hair Follicle Nitric Oxide Synthetase Activity |
| --- | --- |
| $N^G$-methyl-L-arginine | 100% |
| $N^G$-nitro-L-Arginine | 96% |
| $N^G$-nitro-L-arginine methyl ester | 30% |
| $N^G$-nitro-L-arginine benzyl ester | 55% |
| $N\alpha$-acetyl-L-arginine | 39% |
| $N\alpha$-benzoyl-L-argininamide | 100% |
| $N\alpha$-benzoyl-L-arginine methyl ester | 100% |
| $N\alpha$-benzoyl-L-arginine ethyl ester | 100% |
| L-homoarginine | 57% |
| L-argininamide | 98% |

It will be appreciated by those skilled in the art that the invention can be performed within a wide range of equivalent parameters of composition and conditions without departing from the spirit or scope of the invention or of any embodiment thereof.

We claim:

1. A method of reducing mammalian hair growth which comprises selecting an area of skin of a mammal from which hair is growing and from which reduced hair growth is desired; and applying to said area of skin of a mammal from which hair is growing and from which reduced hair growth is desired an inhibitor of nitric oxide synthetase in an amount effective to reduce hair growth.

2. The method of claim 1, wherein said inhibitor is $N^G$-methyl-L-arginine.

3. The method of claim 1, wherein said inhibitor is $N^G$-nitro-L-arginine.

4. The method of claim 1, wherein said inhibitor is $N^G$-nitro-L-arginine methyl ester.

5. The method of claim 1, wherein said inhibitor is $N^G$-nitro-L-arginine benzyl ester.

6. The method of claim 1, wherein said inhibitor is $N\alpha$-acetyl-L-arginine.

7. The method of claim 1, wherein said inhibitor is $N\alpha$-benzoyl-L-arginine.

8. The method of claim 1, wherein said inhibitor is $N\alpha$-benzoyl-L-argininamide.

9. The method of claim 1, wherein said inhibitor is

Nα-benzoyl-L-arginine methyl ester.

10. The method of claim 1, wherein said inhibitor is L-homoarginine.

11. The method of claim 1, wherein said inhibitor is L-argininamide.

12. The method of claim 1, wherein said inhibitor is an irreversible inhibitor.

13. The method of claim 1, wherein said inhibitor is applied as part of a composition comprising a dermatologically acceptable vehicle.

14. The method of claim 13, wherein the concentration of said inhibitor in said composition is between 1% and 30%.

15. The method of claim 13, wherein the composition provides a reduction in hair growth of at least 30% when tested in the Golden Syrian hamster assay.

16. The method of claim 13, wherein the composition provides a reduction in hair growth of at least 50% when tested in the Golden Syrian hamster assay.

17. The method of claim 13, wherein the composition provides a reduction in hair growth of at least 70% when tested in the Golden Syrian hamster assay.

18. The method of claim 1, wherein said inhibitor is applied to the skin in an amount of from 100 to 3000 micrograms of said inhibitor per square centimeter of skin.

19. The method of claim 1, wherein said inhibitor when tested in the hair follicle nitric oxide synthetase inhibition assay inhibits nitric oxide synthetase activity by at least 30%.

20. The method of claim 1, wherein said mammal is a human.

21. The method of claim 1, wherein said area of skin is on the face of the human.

22. The method of claim 1, wherein said area of skin is on a leg of the human.

23. The method of claim 1, wherein said area of skin is on an arm of the human.

24. The method of claim 1, wherein said area of skin is in the armpit of the human.

25. The method of claim 1, wherein said area of skin is on the torso of the human.

* * * * *

UNITED STATES PATENT AND TRADEMARK OFFICE
CERTIFICATE OF CORRECTION

PATENT NO.   : 5,468,476

DATED        : November 21, 1995

INVENTOR(S)  : Gurpreet S. Ahluwalia et al.

It is certified that error appears in the above-identified patent and that said Letters Patent is hereby corrected as shown below:

Column 3, in table 1, col. 1, line 12, "benzoyi" should be --benzoyl--.

Column 3, line 52, after "and" insert --7 min--.

Signed and Sealed this

Twenty-fourth Day of September, 1996

*Attest:*

BRUCE LEHMAN

*Attesting Officer*          Commissioner of Patents and Trademarks